United States Patent [19]
Yamaguchi et al.

[11] Patent Number: 5,180,494
[45] Date of Patent: Jan. 19, 1993

[54] METHOD OF CONTROLLING WASTE WATER TREATMENT BY ANAEROBIC FERMENTATION

[75] Inventors: Makoto Yamaguchi, Tokyo, Japan; John Hake, Oakland, Calif.; Kazuo Okamura; Kiyoshi Minami, both of Tokyo, Japan

[73] Assignee: Shimizu Construction Co., Ltd., Tokyo, Japan

[21] Appl. No.: 593,158

[22] Filed: Oct. 5, 1990

[30] Foreign Application Priority Data

Oct. 9, 1989 [JP] Japan .................................. 1-263762
Oct. 9, 1989 [JP] Japan .................................. 1-263763

[51] Int. Cl.$^5$ ............................................ C02F 11/04
[52] U.S. Cl. ................................ 210/603; 210/614; 210/739
[58] Field of Search ............ 210/603, 609, 614, 739, 210/96.1

[56] References Cited

U.S. PATENT DOCUMENTS

| | | | |
|---|---|---|---|
| 4,659,471 | 4/1987 | Molin et al. | 210/603 |
| 4,663,043 | 5/1987 | Molin et al. | 210/614 |
| 4,986,916 | 1/1991 | Hickey | 210/603 |

Primary Examiner—Thomas Wyse
Attorney, Agent, or Firm—Armstrong & Kubovcik

[57] ABSTRACT

A method for monitoring and regulating waste water treatment by anaerobic fermentation by measuring enzymatic activity or adenosine triphosphate (ATP) concentration. The method provides for earlier detection of abnormal fermentation conditions and allows adjustment of controllable variables prior to the appearance of abnormal effluents.

Also described is an apparatus for controlling waste water treatment by a device which continuously measures the enzyme or ATP concentration in the treated water.

2 Claims, 2 Drawing Sheets

METHOD OF CONTROLLING WASTE WATER TREATMENT BY ANAEROBIC FERMENTATION

BACKGROUND OF THE INVENTION

1. Field of the Invention

The present invention relates to waste water treatment by anaerobic fermentation and, more particularly, to a method of and apparatus for controlling waste water treatment by anaerobic fermentation.

2. Description of the Related Art

Heretofore, waste water treatment in which organic substances that are contained in industrial waste water, sewage sludge, etc. are decomposed by anaerobic bacteria has been employed to treat particularly waste water that has a relatively high concentration of organic substances.

A typical example of the waste water treatment by anaerobic fermentation is methane fermentation, in which organic substances such as carbohydrates, fats and proteins are first decomposed into volatile fatty acids such as acetic acid, propionic acid and butyric acid by the activities of acid-forming bacteria and the like, and then formed into methane gas ($CH_4$) by the activities of methane-forming bacteria. Methane gas may also be formed from methanol, formic acid, acetic acid or carbon dioxide and hydrogen by the activities of methane-forming bacteria.

Anaerobic fermentation treatment is preferably carried out with a maximal operating efficiency. It is, however, necessary in order to increase the operating efficiency to constantly control various fermentation conditions such as temperature, pH, ORP (Oxidation-Reduction Potential), sludge concentration, space loading and the concentration of fermentation inhibitor.

A lowering of the operating efficiency during a waste water treatment by anaerobic fermentation may be known by monitoring various kinds of indicator, for example, a lowering in gasification ($CH_4$), a change in the gas composition (i.e., a decrease in the content of $CH_4$ gas), a change in the pH and ORP in the waste water, total organic carbon (TOC), suspended solid (SS), etc. However, these indicators show only the final results in the anaerobic fermentation tank (reactor).

Accordingly, in an operation based on these indicators, by the time that a lowering in the operating efficiency is recognized, an unfavorable condition in the reactor will have progressed to a considerable extent and a great deal of labor and a large number of days will be needed to return the reactor to the normal, well-conditioned state.

In addition, the measurement of the conventional indicator such as gas composition and TOC needs special, expensive measuring devices, for example, a gas chromatograph and a TOC analyzer.

Incidentally, a method wherein acetic acid or propionic acid in the treated water is measured is known as a technique of relatively high sensitivity, that is, a technique of predicting a lowering in the operating efficiency. It is possible with this method to know a lowering in the operating efficiency in advance. However, this method also needs a special measuring device, for example, a high-pressure liquid chromatograph (HPLC) or gas chromatograph.

Generally speaking, these special devices are costly and necessitate operational training. In addition, since waste water of high concentration is used in the measurement, the maintenance of columns and other associated equipment becomes a serious problem. Further, a long time is needed for the measurement. In particular, high-pressure liquid chromatography (HPLC) and gas chromatography, although highly sensitive, involve the problem that these means are likely to catch a noise and obtain an erroneous value due to a deviation of the standard peak.

The prior art also suffers from the problem that the measuring operation requires much time and labor. For example, high-pressure liquid chromatography (HPLC) needs to inject a standard solution after the replacement of a buffer.

With regard to the temporal relationship between the lowering in the operating efficiency and the acid formation in the reactor in the waste water treatment by anaerobic fermentation, there is such a constant time lag that the operating efficiency begins to lower after a predetermined time has elapsed since the rate of acid formation began to increase. More specifically, in an ordinary plant-scale operation the operating efficiency begins to lower after about one week has elaspsed since the rate of acid formation began to increase. This means that a future lowering in the operating efficiency can be predicted about one week before the operating efficiency actually lowers by monitoring the acid formation condition.

However, the above-described time lag is not sufficiently long to control various fermentation conditions so as to prevent a lowering in the operating efficiency of the reactor.

More specifically, even if an operation of controlling various fermentation conditions is initiated after an increase in the rate of acid formation is found, it will be too late for completely preventing a lowering in the operating efficiency.

The necessity for "early discovery and early treatment", which is said as to the human health care, also applies to the field of waste water treatment by anaerobic fermentation.

Under these circumstances, it has been desired to develop a means which enables prediction of a lowering in the anaerobic fermentation operating efficiency in advance of the increase in the rate of acid formation.

It has also heretofore been difficult to judge whether or not a slight peak of acetic acid or methanol in the first stages of lowering in the operating efficiency is a noise.

Further, the construction of methane fermentation tanks is easier in a rural area than in an urban area from the viewpoint of land prices, environmental problems and so forth; however, the maintenance of precision machinery (i.e., the replacement of parts, trouble shooting and machine adjustment service) at such a rural area is not easy.

Accordingly, it has been strongly demanded to provide a means which enables prediction of a lowering in the operating efficiency in an anaerobic fermentation system earlier, readily, inexpensively, sensitively, stably and reliably.

SUMMARY OF THE INVENTION

In view of the present state of waste water treatment by anaerobic fermentation, the present inventors conducted exhaustive studies in order to solve the above-described problems.

In the process of our studies, we collected waste water samples from a thermophilic methanogenic digestion tank in a normal state where methanol was a main carbon source as in the case of kraftpulp manufacture industry sewage and from a thermophilic digestion tank in an abnormal state where acetic acid, propionic acid, etc. had already appeared, and measured ① the activities of enzymes and the concentration of adenosine triphosphate (ATP) in "raw water" and ② the enzyme activity of various kinds of enzyme in "the solid content (mainly microorganisms) in the raw water" after centrifugal separation, together with a change (rise or fall) in the adenosine triphosphate (ATP) concentration.

As a result, the present inventors have found that, among the various enzymes, "acid phosphatase", "alkaline phosphatase", "various kinds of transaminase", "amylase" and so forth can serve as highly sensitive indicators which are useful to judge whether a particular fermentation condition is good or bad and that ATP can also serve as a highly sensitive indicator useful for the judgement of a fermentation condition.

More specifically, the present inventors have discovered that the activity of the above-described enzymes and the ATP concentration are recognized to be increasing in a stage which is considerably ahead of the time of appearance of organic acids such as acetic acid, propionic acid, etc. in the process of anaerobic fermentation, as described later in specific Examples. As is generally known, ATP is a compound that participates in various kinds of energy metabolism as an energy carrier in organisms and hence plays an important part in the acquisition and utilization of energy.

The studies conducted by the present inventors have also revealed that these indicators are superior in sensitivity to any of those which have heretofore been used. More specifically, the above-described enzymes and ATP serve as indicators which enable prediction of a lowering in the operating efficiency in the reactor earlier than any of the conventional indicators, for example, the time at which the rate of generation of methane gas changes, or the time at which the rate of acid formation changes.

For example, in a plant-scale reactor for waste water treatment by anaerobic fermentation, the point of time when the rate of acid formation begins to increase is about one week before the operating efficiency begins to lower, whereas, the formation of the above-described enzymes and ATP occurs noticeably about three to four weeks before the operating efficiency begins to lower.

The present invention, which has been accomplished on the basis of the above-described finding, provides (1) a method of controlling waste water treatment by anaerobic fermentation, which comprises continuously measuring the enzyme activity or ATP concentration in the water treated by the anaerobic fermentation and controlling various fermentation conditions as occasion demands on the basis of the result of the measurement, and also provides (2) an apparatus for controlling waste water treatment by anaerobic fermentation, which comprises a device that continuously measures the enzyme activity or ATP concentration in the water treated in an anaerobic fermentation tank.

Unlike the conventional method of controlling waste water treatment by anaerobic fermentation, which is based on a physicochemical measurement, the present invention controls waste water treatment by anaerobic fermentation by biochemically measuring an active condition of microorganisms in the reactor in terms of the enzyme activity or the ATP concentration.

According to the present invention, the fact that the condition in the reactor is proceeding to an abnormal state can be predicted earlier than in the case of the prior art. It is therefore possible to carry out earlier the control of various fermentation conditions, so that even if an abnormality begins to occur in the fermentation conditions of the waste water treated in the fermentation tank, the fermentation conditions can be returned to normal with ease and within a short period of time.

The measurement itself is simple and less costly and needs neither special device (the measurement being capable of being effected with a simple spectrophotometer or visual observation, for example) nor special skill, so that accurate data can be obtained at once even by an unskilled person. By feeding back the result of the measurement to control various fermentation conditions, the waste water treatment in the anaerobic fermentation tank can be controlled to and maintained in optimal conditions speedily, easily and precisely. As a result, it is possible to maintain highly efficient fermentation treatment, which is carried out in the waste water treatment tank by anaerobic fermentation, for a long period of time.

It should be noted that the method of the present invention may be used together with the conventional method to obtain even more accurate data and execute an even more excellent waste water treating operation.

Technical matters which are relevant to the present invention will next be explained.

① Mechanism of Lowering in Operating Efficiency of Methane Fermentation

This is equivalent to a lowering in the rate of generation of methane gas, which is directly attributable to a lowering in the activity of methane-forming bacteria (that is, a lowering in the activity of methane-forming bacteria, extinction thereof, a decrease in the number of methane-forming bacteria, etc.).

On the other hand, a lowering in the activity of methane-forming bacteria invites a rise in the activity (including an increase in the number of bacteria) of acid-forming bacteria (i.e., bacteria that participate in formation of volatile fatty acids such as acetic acid, propionic acid, etc.). Thus, there is also the following relativity:

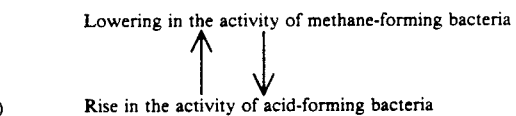

Lowering in the activity of methane-forming bacteria

Rise in the activity of acid-forming bacteria

It is therefore also possible to predict a change in the operating efficiency of methane fermentation by detecting a degree to which acid-forming bacteria have been activated.

② Measurement of Various Indicators Concerned with Operating Efficiency of Methane Fermentation As has been described above, the prior art measures as indicators a lowering in the rate of generation of gas ($CH_4$), a change in the gas composition (a reduction in the $CH_4$ gas content), changes in the pH and ORP of the waste water, an increase in the total organic carbon (TOC), suspended solid (SS), etc. These indicators are, however, the final results inside the fermentation tank (reactor).

Accordingly, the measurement of these indicators involves a considerable time lag from the initial change (i.e., for example, a change of a polymeric organic substance in the waste water into a monomeric substance). Therefore, in an operation based on these indicators, by the time that a lowering in the operating efficiency is recognized, an unfavorable condition in the reactor will have progressed to a considerable extent and a great deal of time and labor will be needed to return the reactor to the normal state of fermentation conditions.

Under these circumstances, the present inventors noted enzymes, such as polymer decomposing enzymes (e.g., amylase) and enzymes that are related to the formation of acids, together with ATP, which act in the first stages of the change of organic substances into volatile fatty acids during the waste water treatment by anaerobic fermentation.

Generally speaking, in the waste water treatment by methane fermentation, enzymes (polymer decomposing enzymes and enzymes related to the formation of acids) participate in the process:

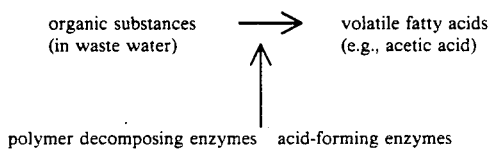

Next, methane (gas)-forming enzymes participate in the process:

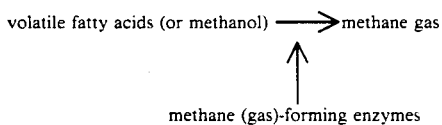

(3) Difference in the Metabolic Pathway Between Methane-Forming Bacteria (Archaebacteria) and Bacteria (Mainly, Eubacteria) in the Reactor in an Abnormal State In general, methane-forming bacteria form methane from relatively simple compounds (methanol, $H_2 + CO_2$), formic acid, acetic acid, methylamine, etc.) and therefore can live without depending upon complex organic compounds except for vitamins.

It is also considered that, unlike other general bacteria (eubacteria), methane-forming bacteria have no enzyme system that decomposes complex organic compounds into simple compounds. In addition, unlike other bacteria, methane bacteria have no peptidoglycan layer in the cell wall. That is, methane-forming bacteria contain no peptidoglycan forming enzyme.

Further, with regard to methane-forming bacteria, the activity of metabolic enzymes and the ATP concentration, which are common to all bacteria, are considered to be relatively low.

It is therefore expected that the activity of polymer decomposing enzymes (e.g., amylase) and matabolic enzymes (e.g., acid phosphatase, alkaline phosphatase, transaminase, etc.) and the ATP concentration, which are common to all bacteria, will be higher at the time when the methane fermentation is in an abnormal state (in addition, eubacteria may be considered to be predominant in the reactor) than at the time when the methane fermentation is in a normal state (methane-forming bacteria is predominant).

Accordingly, by monitoring a rise in the activity of these enzymes as being indicators, a lowering in the operating efficiency of the methane fermentation can be readily predicted.

For the reasons stated in ①  to ③ according to the present invention, the concentrations of polymer decomposing enzymes, acid-forming enzymes, methane-forming enzymes, metabolic enzyme and ATP are measured and various conditions, such as the pH, ORP, space loading and organic matter concentration, are controlled on the basis of the results of the measurement, thereby correcting an abnormal state which is expected to occur and avoiding the occurrence of any abnormality, and thus enabling a normal operation to continue over a long period of time.

With a view to measuring variations in the enzyme activity with high sensitivity, it is preferable to adopt a method that employs a specific substrate (colorimetric system), which is a simple and easy method that is commonly used in the field of clinical medicine. With this method, it is possible to amplify variations in the enzyme activity. Therefore, the detection of enzymes by using antibody against them is useful.

To measure variations in the ATP concentration with high sensitivity, it is preferable to adopt, for example, a method that employs a specific substrate (colorimetric system) of luciferin-luciferase system, which is a known simple and easy measuring method. This method enables amplification of variations in the ATP concentration.

Other measures may be taken to prevent lowering in the operating efficiency, in addition to the above-described measurement of an absolute value of the enzyme activity or other indicators. For example, the enzyme activity may be measured in the form of a differential value as a rate of change to effect feedback control. This method is preferable from the viewpoint of capability of speedily and accurately coping with a predicted lowering in the operating efficiency.

Although in the foregoing four kinds of enzyme (i.e., amylase, acid phosphatase, alkaline phosphatase and transaminase) and ATP are mentioned as preferable indicators, it is also possible to employ in the present invention various other enzymes, such as peptidoglycan synthetases, metabolic enzymes that produce energy from proteins, fats and polysaccharide, and various other common enzymes, for example, those which are present in archaebacteria and eubacteria.

Although in the experiments the present inventors studied a mesophilic methane fermentation (i.e., methane-forming bacteria belonging to genus Methanolobus) and a thermophilic methane fermentation (i.e., methane-forming bacteria belonging to genus Methanosarcina), in which methanol in kraftpulp manufacture industry sewage was a carbon source, the present invention may also be applied to other waste water fermentation treatment by known thermophilic, mesophilic and psychrophilic bacteria, such as those mentioned below, which participate in ordinary methane fermentation systems:

Genera Methanobacterium, Methanobrevibacter and Methanosphaera (Methanobacteriaceae family); Methanothermus (Methanothermaceae family); Methanococcus (Methanococcaceae family); Methanomicrobium, Methanogenium and Methanospirillum (Methanomicrobiaceae family); Methanoplanus (Methanoplanaceae family); Methanosarcina and Methanothrix (Methanosarcinaceae family); Methanolobus; Methanococcoides; Methanohalophilus; Methanocorpasculum; and Methanohalobium.

It should be noted that, in an industrial application of the present invention, it is preferable to use a biosensor or a biochip which can measure the enzyme activity in waste water, and to automate the control process by utilizing an automatic sampling system and an automatic measuring system, which are generally employed in the clinical field.

DETAILED DESCRIPTION OF THE INVENTION

One embodiment of the present invention will be described below in detail with reference to the accompanying drawings.

Figure 1:
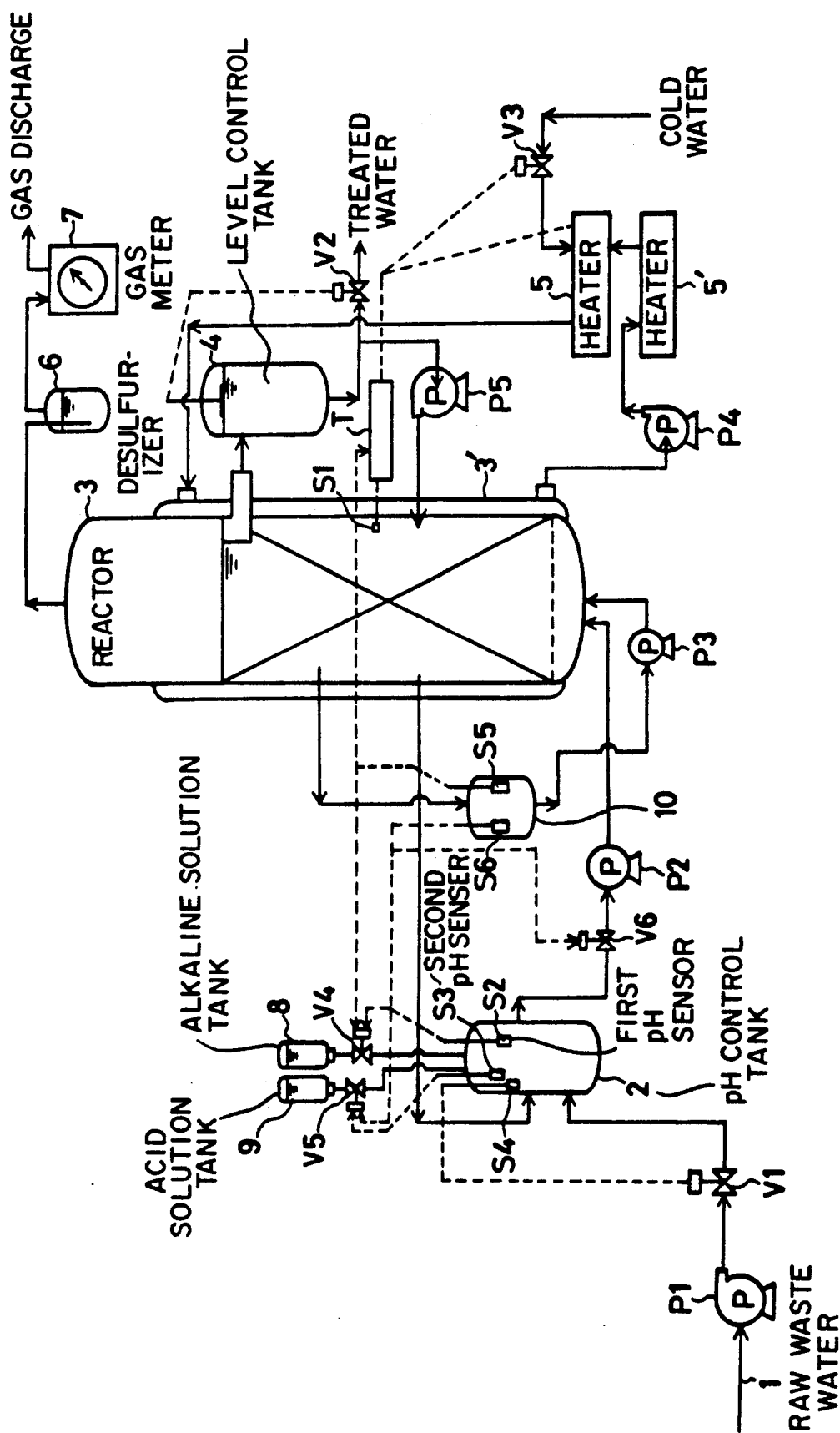
FIG. 1 is a block diagram showing one embodiment of the apparatus according to the present invention.

Referring first to FIG. 1, which is a block diagram showing one embodiment of the apparatus according to the present invention, reference numeral 1 denotes a raw waste water supply pipe, 2 a pH control tank, 3 an anaerobic fermentation tank (reactor), 3' a thermostatic chamber, 4 a level control tank, 5 and 5' heaters, 6 a desulfurizer, 7 a gas meter, 8 an alkaline solution tank, 9 an acid solution tank, 10 an enzyme or ATP measuring tank, P1 to P5 pumps, V1 to V6 solenoid valves, and S1 to S6 various sensors.

The operation of the waste water treating apparatus by anaerobic fermentation will next be explained.

First, raw waste water flowing through the supply pipe 1 enters the pH control tank 2 and is then introduced into the anaerobic fermentation tank 3.

On the way to the anaerobic fermentation tank 3, the raw waste water passes through the first pump P1, the first solenoid valve V1, the sixth solenoid valve V6 and the second pump P2.

In the anaerobic fermentation tank 3, bacteria such as anaerobic ferment bacteria (e.g., methane-forming bacteria) are growing, so that organic components (mainly, BOD components) in the raw waste water are consumed, thereby purifying the waste water.

Produced biogas (e.g., methane gas) is led out from the top of the anaerobic fermentation tank 3 to the desulfurizer 6 where hydrogen sulfide is removed from the biogas, and then passed through the gas meter 7 and accumulated in a gas holder (not shown).

The anaerobic fermentation tank 3 is surrounded by the thermostatic chamber 3' so that the fermented liquid inside the tank 3 is constantly controlled at an appropriate fermentation temperature. The temperature control is effected by opening and closing the solenoid valve V3 or turning on and off the heater 5 in response to a signal from the temperature sensor S1.

The level of the fermented liquid in the anaerobic fermentation tank 3 is controlled by discharging the treated water by the operation of the level control tank 4 that is provided with the second solenoid valve V2.

Circulation of the fermented liquid in the anaerobic fermentation tank 3 is conducted mainly by ① a system that comprises the level control tank 4 → the fifth pump P5 → the anaerobic fermentation tank 3 and ② a system that comprises the anaerobic fermentation tank 3 → the pH control tank 2 → the second pump P2 → the anaerobic fermentation tank 3 and also performed a little by ③ a system that comprises the enzyme or ATP measuring tank 10 → the third pumpe P3 → the anaerobic fermentation tank 3.

In the enzyme or ATP measuring tank 10, the concentrations of polymer decomposing enzymes (e.g., amylase), common enzymes (e.g., acid phosphatase, alkaline phosphatase and transaminase) and ATP are measured with a biosensor or by a colorimetry using a reagent, which is carried out after the liquid sampling process.

The result of the measurement is sent in the form of an electric signal to the solenoid valve V4 of the alkaline solution tank 8, the solenoid valve V5 of the acid solution tank 9, the solenoid V6 or a temperature setting device T to open or close the valve concerned or set a specific temperature, thereby executing control and management of optimal fermentation conditions in the anaerobic fermentation tank 3. In addition, the electric signal representative of the result of the measurement may be sent to the valve V1 for controlling the supply of raw waste water to control the degree of opening of the valve V1.

Although in this embodiment the sampling and measurement are carried out at the fermentation tank, it should be noted that the arrangement may be such that an automatic measuring device is installed in a receiver tank or a treated water pipe and the result of the measurement is fed back to control fermentation conditions.

In this embodiment, a 200 l methane fermentation tank (reactor) 3 was employed, and methane fermentation treatment was carried out at a high temperature of 55° C. with a medium containing methanol as a main carbon source.

In order to artificially cause a lowering in the operating efficiency during the fermentation process, waste water with a high methanol concentration was employed as a liquid to be treated, and essential nutrient sources (for example, N, P and K sources) were removed from the medium or a fermentation inhibitor (for example, a coenzyme analog) was added thereto.

Regarding the Measurement of the Enzyme Activity of the ATP Concentration

The measurement of the enzyme activity or the ATP concentration in a chromophoric system that employs a chromophoric substrate is widely adopted in the field of clinical chemistry and can be carried out extremely easily. In this embodiment, however, alkaline phosphatase and acid phosphatase were measured by Kind-King method, transaminase by Reitman-Frankel method, amylase by Marchall J. L. et al., and the ATP concentration by a method employing a specific substrate (chromophoric system) of luciferin-luciferase system.

After the color development, the activity of each enzyme was measured with a spectrophotometer at the maximum absorption wavelength thereof.

Regarding the Preparation of Samples

① Preparation of a Sample of the Treated Water from the Reactor:

The sampled treated water was subjected to centrifugal separation or passed through a 0.45 um filter, and the resulting supernatant or the water that passed through the filter was used.

It should be noted that, since a turbidity in a sample in the measurement of the enzyme activity or ATP concentration in a chromophoric system appears to be pseudo-positive, centrifugal separation or filtration is needed.

② Preparation of a Sample of the Precipitate in the Treated Water from the Reactor:

The sample treated water was centrifugally separated, and the resulting precipitate (mainly containing microorganisms) was collected.

5 ml of precipitate was subjected to ultrasonication for 3 minutes under the conditions of 20 kHz and 130 W to crush cells and then subjected to centrifugal separation. The resulting supernatant was employed as an enzyme measuring solution or an ATP concentration measuring solution.

EXPERIMENTAL EXAMPLE 1

Table 1 below shows the rate of gas generation and various properties of the treated water in a normal state and an abnormal state.

TABLE 1

|   | Normal | Abnormal |
|---|---|---|
| TOC (mg/l) | 250 | 840 |
| Acetic acid (mg/l) | 0 | 1600 |
| Propionic acid (mg/l) | 0 | 150 |
| Methanol (mg/l) | 0 | 280 |
| Acid phosphatase[1] | 1 | scores of times |
| Alkaline phosphatase[1] | 1 | ten-odd times |
| Amylase[1] | 1 | ten-odd times |
| Transaminase[1] | 1 | ten-odd times |
| ATP | 1 | scores of times |
| Gasification (l/d) | 400 | 300 |

[1] the specific activity in an abnormal state in the case where the activity in a normal state is determined to be "1".

The above results were obtained by carrying out high-temperature (thermophilic) digestive treatment on waste water containing methanol as a main carbon source at a TOC loading of about 230 g/day. The sample that was employed for the measurement was an enzyme or ATP measuring solution obtained by the method stated in the sample preparation ②.

It will be clear from the results shown in Table 1 that, when the methane fermentation treatment is in an abnormal state, there are increases not only in the leakage of methanol, acetic acid and propionic acid but also in the enzyme activity of the four different kinds of enzyme and the ATP concentration.

EXPERIMENTAL EXAMPLE 2

Figure 2:
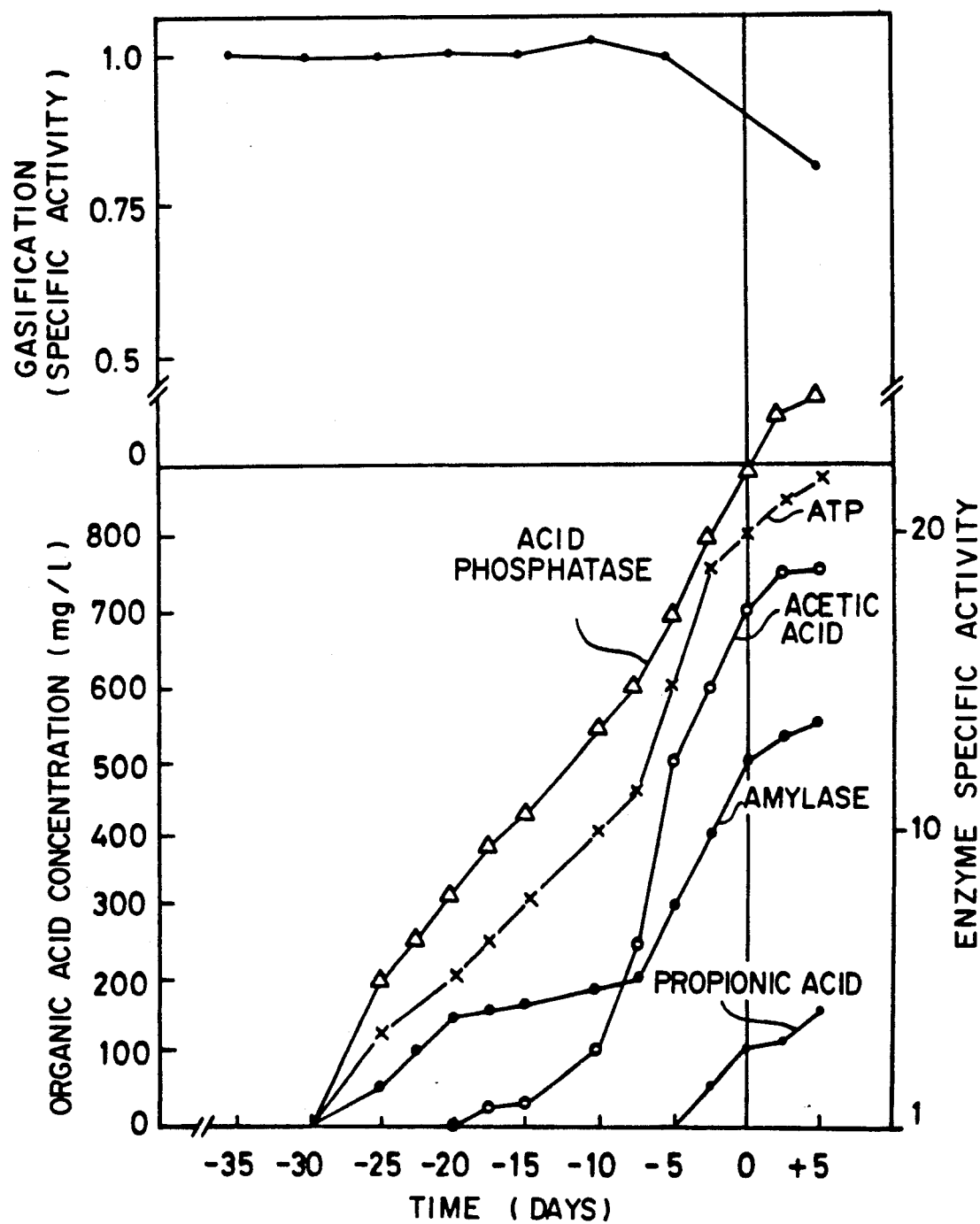
FIG. 2 is a graph showing changes with time of the values of various components of the effluent flowing out of an anaerobic fermentation tank.

An enzyme measuring solution obtained by the sample preparation method ② in the same way as in Experimental Example 1 was measured. FIG. 2 shows changes with time of the properties of the liquid being treated in the reactor on the basis of the results of the measurement.

It should be noted that in the figure the gasification, the enzyme activity and the ATP concentration are each shown on a scale where the value in a normal state is determined to be "1". In the figure, the day when the gas generation rate actually began to lower is shown to be "0".

It will be understood from FIG. 2 that the enzyme activity of acid phosphatase and amylase and the ATP concentration had already begun to rise at least 10 days before the appearance of acetic acid or other volatile fatty acids.

Accordingly, it will be understood that the change in the enzyme activity or the ATP concentration can serve as a considerably excellent indicator for prediction of the occurrence of an abnormality in the reactor.

Although in the above Experimental Examples 1 and 2 experiments were carried out on waste water containing methanol as a main carbon source, results similar to those shown in Table 1 and FIG. 2 were obtained in experiments carried out on general waste water containing organic substances, such as carbohydrates, fats and proteins, as main carbon sources.

As has been detailed above, it is possible according to the present invention to predict a lowering in the operating efficiency of the waste water treatment by anaerobic fermentation a considerably long time ahead of the time at which the lowering in the operating efficiency occurs. In addition, it is possible to effect the prediction with a simple and easy measuring means within a short time and with high sensitivity as well as stably and reliably. By feeding back the results of the measurement, various fermentation conditions can be precontrolled.

Accordingly, the present invention, in which various fermentation conditions are precontrolled on the basis of the measured enzyme activity or ATP data, enables efficient and excellent waste water treatment to continue over a long period of time while constantly and stably maintaining optimal anaerobic fermentation conditions.

We claim:

1. A method of controlling waste water treatment by anaerobic fermentation, comprising:
   continuously measuring the enzyme activity in the water treated by the anaerobic fermentation; and
   controlling various fermentation conditions as occasion demands on the basis of the result of the measurement.

2. A method of controlling waste water treatment by anaerobic fermentation according to claim 1, wherein said anaerobic fermentation is methane fermentation.

* * * * *